US011653829B2

(12) United States Patent
Mikaelian

(10) Patent No.: US 11,653,829 B2
(45) Date of Patent: May 23, 2023

(54) SYSTEMS AND METHODS FOR PERFORMING AUTOMATED SUBJECTIVE REFRACTION

(71) Applicant: NIDEK CO., LTD., Aichi (JP)

(72) Inventor: Gareguin Mikaelian, San Pedro, CA (US)

(73) Assignee: NIDEK CO., LTD., Aichi (JP)

( * ) Notice: Subject to any disclaimer, the term of this patent is extended or adjusted under 35 U.S.C. 154(b) by 18 days.

(21) Appl. No.: 17/119,613

(22) Filed: Dec. 11, 2020

(65) Prior Publication Data
US 2021/0177254 A1 Jun. 17, 2021

Related U.S. Application Data

(60) Provisional application No. 62/949,015, filed on Dec. 17, 2019.

(51) Int. Cl.
*A61B 3/028* (2006.01)
*A61B 3/00* (2006.01)
*A61B 3/036* (2006.01)
*A61B 3/02* (2006.01)
*A61B 3/032* (2006.01)

(52) U.S. Cl.
CPC .......... *A61B 3/0285* (2013.01); *A61B 3/0033* (2013.01); *A61B 3/022* (2013.01); *A61B 3/032* (2013.01); *A61B 3/036* (2013.01)

(58) Field of Classification Search
CPC ..... A61B 3/0285; A61B 3/0033; A61B 3/022; A61B 3/032; A61B 3/036
See application file for complete search history.

(56) References Cited

U.S. PATENT DOCUMENTS

| 2002/0047987 | A1* | 4/2002 | Massengill | G02B 27/0172 351/204 |
| 2010/0110379 | A1* | 5/2010 | Zhou | A61B 3/14 351/205 |
| 2012/0120369 | A1* | 5/2012 | Lai | A61B 3/0091 351/239 |
| 2013/0182224 | A1* | 7/2013 | Schwiegerling | G02B 5/32 351/234 |
| 2017/0079524 | A1* | 3/2017 | Bex | A61B 3/032 |

FOREIGN PATENT DOCUMENTS

WO WO-2004072687 A2 * 8/2004 ........... A61B 3/0285

* cited by examiner

*Primary Examiner* — William R Alexander
*Assistant Examiner* — Sharrief I Broome
(74) *Attorney, Agent, or Firm* — Rankin, Hill & Clark LLP

(57) ABSTRACT

A method of performing an optometric examination of a patient includes positioning the patient behind a phoropter; presenting visual stimuli to the patient using a computer-controlled device; recording the patient's response to the stimuli; automatically adjusting the settings of the phoropter to improve one or more characteristics of the patient's vision; and automatically determining the prescription for the refractive error correction for the patient.

20 Claims, 5 Drawing Sheets

SYSTEMS AND METHODS FOR PERFORMING AUTOMATED SUBJECTIVE REFRACTION

TECHNICAL FIELD

The present disclosure relates to performing optometric examination, specifically automated refraction.

BACKGROUND

Subjective examination with a phoropter is widely used due to the accuracy in determining an appropriate correction of a refractive error for a patient. The patient is usually seated so that he or she can view an eye chart or a screen located at a certain distance. The phoropter is positioned so that the patient is able to view the said eye chart or the screen through the lenses in the phoropter. The examiner then adjusts the lens combination manually or through electronic interface, while continuously getting feedback from the patient regarding the ability of the patient to see and identify different letters or objects on the eye chart or on the screen. Often, the goal of a phoropter examination is to select the spherical and cylindrical power combination of the lenses, to correct the refractive errors in the eye and to optimize visual acuity of the patient for the far viewing distance. Because constant communication between the healthcare practitioner and the patient is involved, and many times the patient is unsure about the proper selection between various lens combinations, a typical phoropter examination is often performed by a well-trained healthcare practitioner. A phoropter examination could be a time-consuming procedure, even with modern electronic phoropters. Furthermore, often patients feel rushed and pressured to quickly provide the correct answer, which may generate unnecessary anxiety in the patient. Reducing the operator time and maximally automating the phoropter examination and selection of corrective lens for a patient may be a valuable proposition in optometric and ophthalmic practices. The ability to perform automated phoropter examination in which the operator involvement is minimized or is not required may be beneficial to the optometric or ophthalmic practice and may be performed at locations where a trained phoropter operators are not available.

BRIEF DESCRIPTION

According to one aspect, a device for performing subjective refraction examination with minimal operator involvement.

In one aspect the lens selection in a phoropter is controlled by the patient.

In another aspect of the disclosure an automated threshold-based test of the visual acuity is performed in conjunction with automated changes in phoropter lenses.

In another aspect of the disclosure an automated threshold-based test of the visual acuity is performed while the patient is controlling the lens selection in a phoropter.

In yet another aspect of the disclosure a test of visual acuity is performed while the patient is controlling some parameters or lens selections of the phoropter.

In another aspect of the invention the phoropter is coupled with an eye chart that is capable of displaying visual stimuli of various sizes and/or contrast values.

DETAILED DESCRIPTION

Problems to be Solved by the Invention

The present disclosure is directed towards systems and methods for performing accurate evaluation of the eye, including determining the appropriate vision correction for a patient.

Commonly, subjective refraction is performed using a phoropter. The patient is positioned in front of an eye chart and a phoropter is placed in front of the patient's eyes. The healthcare practitioner then adjusts the lens combination in the phoropter to optimize the vision and estimate the power and cylinder required for achieving refractive correction. The best corrected visual acuity (BCVA) is a measure of visual acuity that can be achieved using a phoropter.

In general, the phoropter examination comprises of two steps. In the first step the practitioner determines the sphere value that maximally improves the far vision. In the second step the practitioner evaluates the optimal cylinder correction including the cylinder power and orientation angle.

In some cases, the phoropter examination is preceded by an objective measurement of the refraction, wherein the patient's refraction is measured using an autorefractor, wavefront aberrometer, or another refraction measuring instrument. In such cases the instrument output may be used to determine the starting point of the phoropter examination and to save time in selecting the lenses.

In many cases, the final spectacle prescription is different from the lens configuration in the phoropter that was used to achieve BCVA. Some physicians may prefer to undercorrect the cylinder, and some are taught that the minus spectacle power should be "treated as money" and given out to the patient only when necessary. Thus, the outcome of the phoropter examination may strongly depend on the person performing the exam and may vary from one practitioner to another.

It may be beneficial to eliminate the inter-operator variability of a phoropter examination by developing an automated phoropter, which may use inputs from a patient to determine the configuration of the lenses in the phoropter, BCVA, prescription, other vision parameters, or any combination of the above.

Figure 1:
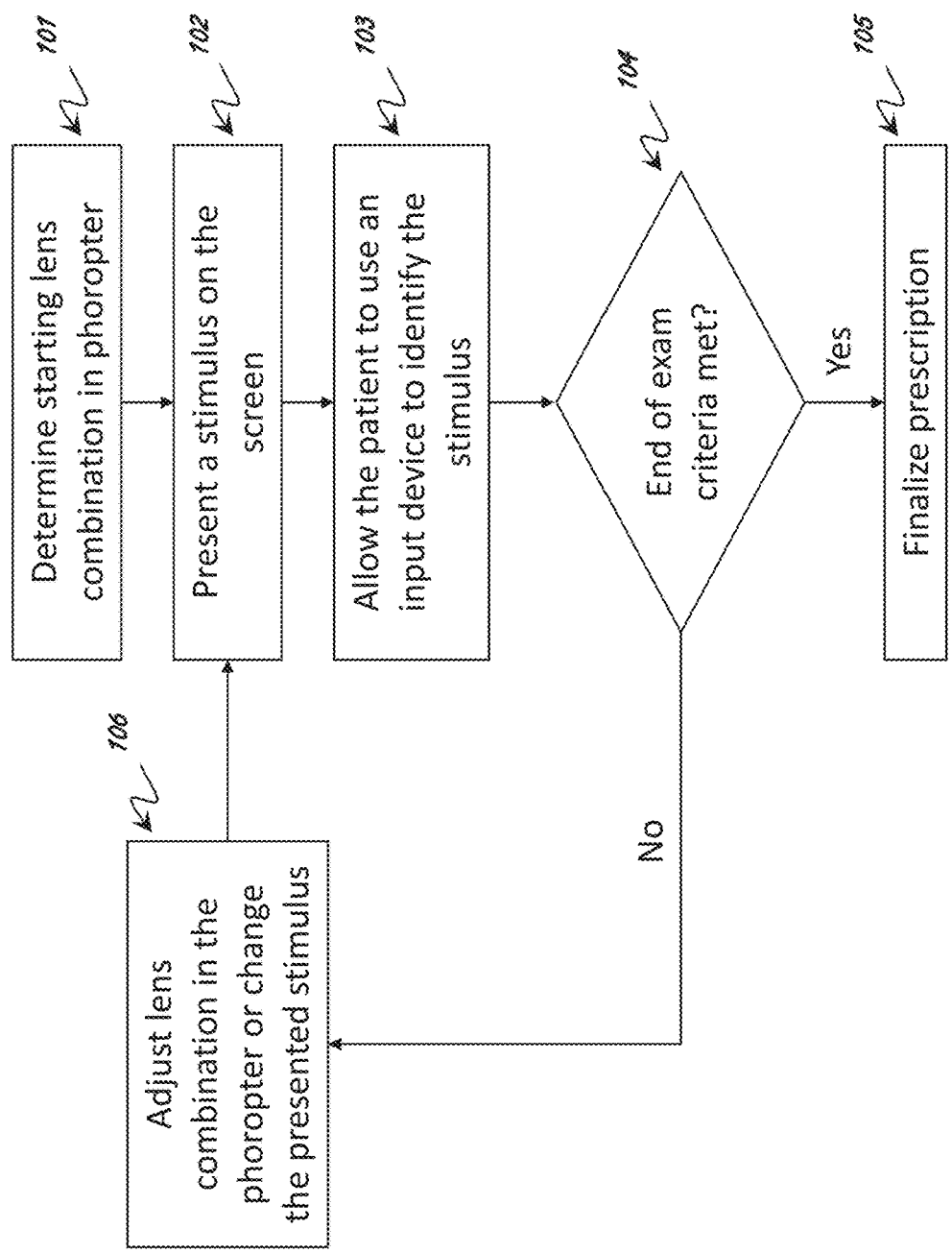
FIG. 1 is an illustration of a flow diagram of an automated phoropter examination.

The schematic diagram illustrating the exam flow in such automated phoropter is shown in FIG. 1. The starting lens combination 101 may be hard coded on the device, or it may be determined for a specific patient by utilizing prior prescription, measuring the patient's prior lenses, automated refraction measurement, demographic data, or any other method. In general, it may be advantageous to start the automated examination with a phoropter lens combination that is close to the patient's refractive error. The end of exam criteria 104 may be specified in terms of BCVA, visual acuity (VA) number of completed cycles, amount of improvement in each subsequent iteration, or by any other means.

In some aspects it is beneficial to perform a threshold-based visual acuity evaluation while adjusting the lens combination in the phoropter. In threshold-based examination various size stimuli are presented and a psychometric function is evaluated. In such types of vision evaluation, the threshold, slope, or both parameters can be estimated or measured. In such aspect the end of exam criteria 104 may be specified by a threshold or slope value of the psychometric function.

In some aspects it is beneficial to use an input device to record patient's entries. Such device can be a specially designed device, speech recognition software, touch screen, gamepad controller, or another input device commonly used for video games or other computer applications.

In one aspect of the invention a Landolt C or tumbling E of various sizes and orientations may be presented to the patient. In this aspect the patient may use one side of the input device to indicate the orientation of the Landolt C or tumbling E. It may also be beneficial to allow the patient to control the lens configuration in the phoropter using the buttons on the other side of the input device. In one example, one hand of the patient may be used to determine the stimulus orientation, while the other hand may be used to control the lens combination in the phoropter.

In some aspects of the invention the visual acuity examination may be presented as a game, where the BCVA score is presented to the patient in real time and his or her goal is to get the highest score possible by correctly identifying the orientation of the Landolt C and by selecting the best combination of the lenses in the phoropter. In such aspect the visual stimuli may be presented as a part of a computer game designed to engage the patient, while simultaneously performing a vision examination. This may be achieved by inducing the patient to maximize his or her score by improving the vision of the said patient through properly selected phoropter lens combination.

It may be beneficial to input the starting refraction parameters into the system from a measurement performed by an autorefractor, retinoscope, aberrometer, or by reading the refraction of patient's habitual glasses.

Figure 2:
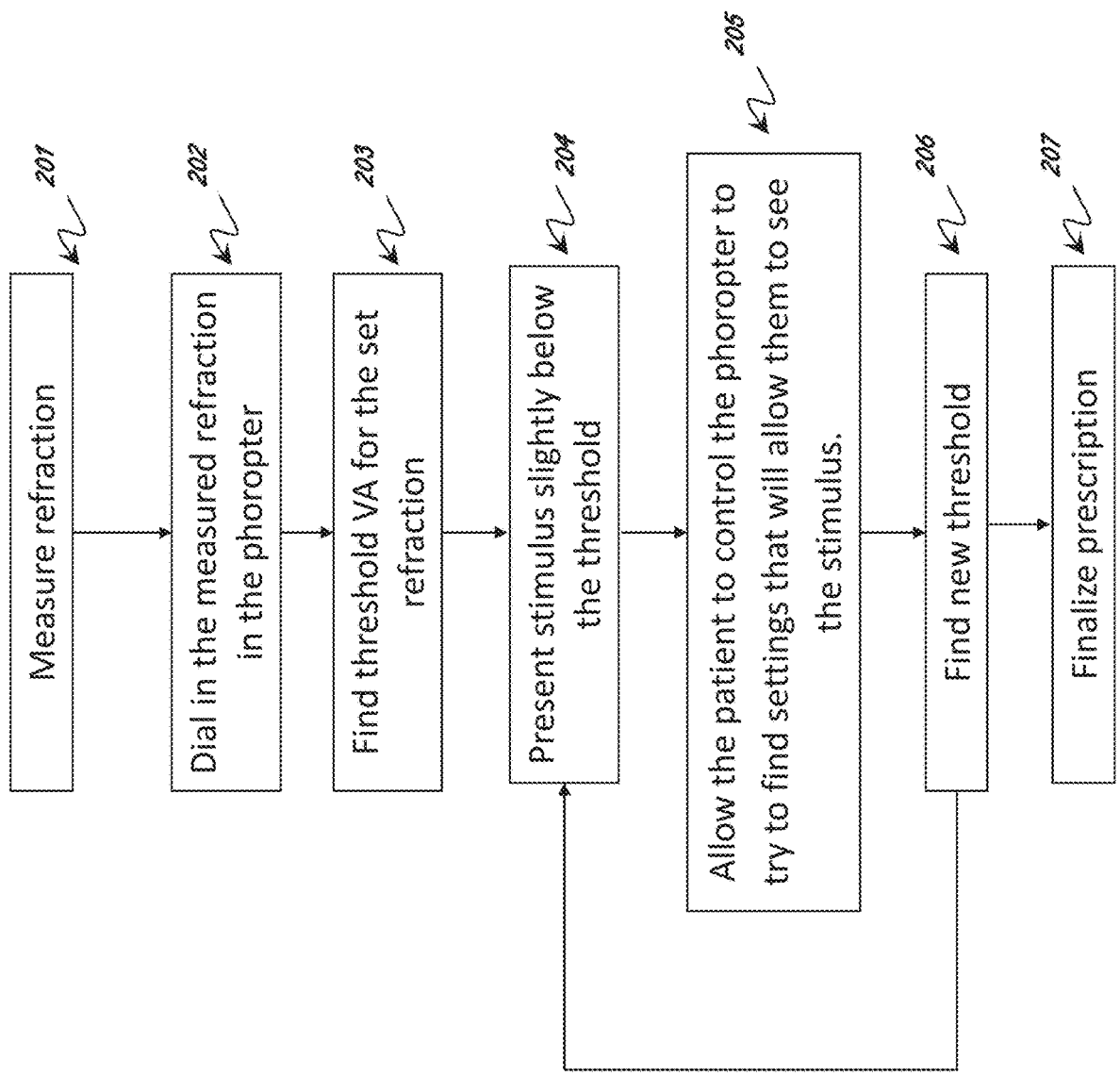
FIG. 2 is an illustration of a flow diagram of an automated phoropter examination for threshold based determination of refractive error correction.

In one aspect an examination may be performed in a following sequence of steps (FIG. 2.):
1. Measure refraction 201
2. Dial in the measured refraction into the phoropter 202
3. Find the threshold VA for the set refraction 203
4. Present stimulus slightly below threshold 204
5. Allow the patient to control the phoropter using left set of buttons on the game controller to try to find settings that will allow them to see the stimulus 205
6. Once patient thinks they can see the stimulus, find new threshold 206
7. Go to step 4 and repeat until there is no improvement
8. Finalize the prescription 207

In the above sequence, it may be possible to skip one or several of the steps.

Figure 3:
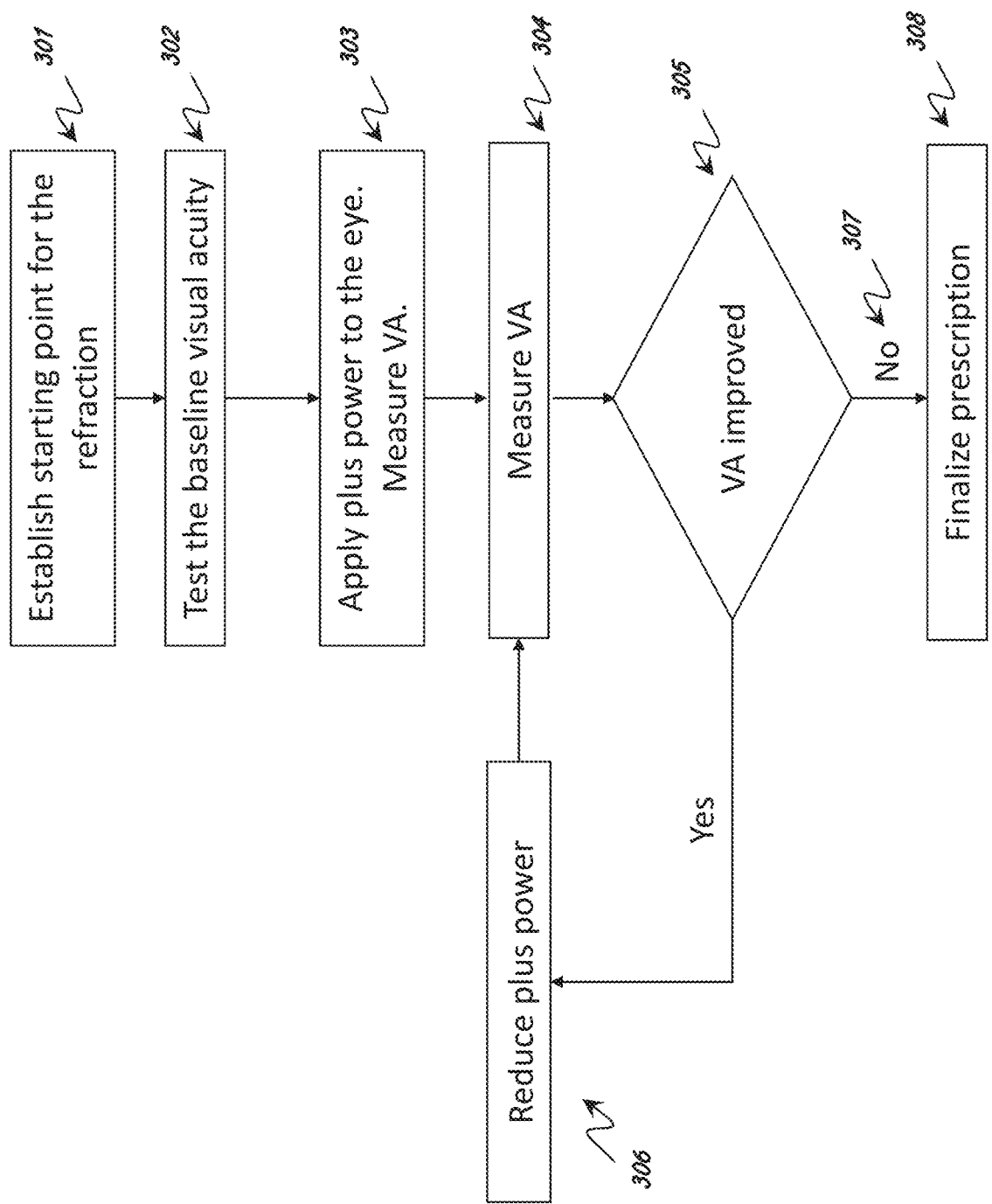
FIG. 3 is an illustration of a flow diagram of an automated phoropter examination for determination of refractive error correction.

Alternatively, it may be possible to simulate the actions of the optometrist during the subjective refraction using a phoropter. FIG. 3 illustrates one such possible method for automated refraction:
1. Establish a starting point for the refraction using an autorefractor reading, retinoscopy, or measurement of patient's spectacle power 301
2. Test the baseline visual acuity. This step may be performed using existing threshold-based algorithms. At this point the threshold algorithms will measure the threshold value and the slope of the psychometric function. 302
3. Apply plus power to the tested eye. 303
4. Measure visual acuity with few Landolt C presentations. 304
5. Continue reducing the applied power 306 until measured VA stops improving.
6. The sphere power at which VA stops improving should be the prescription.

Figure 4:
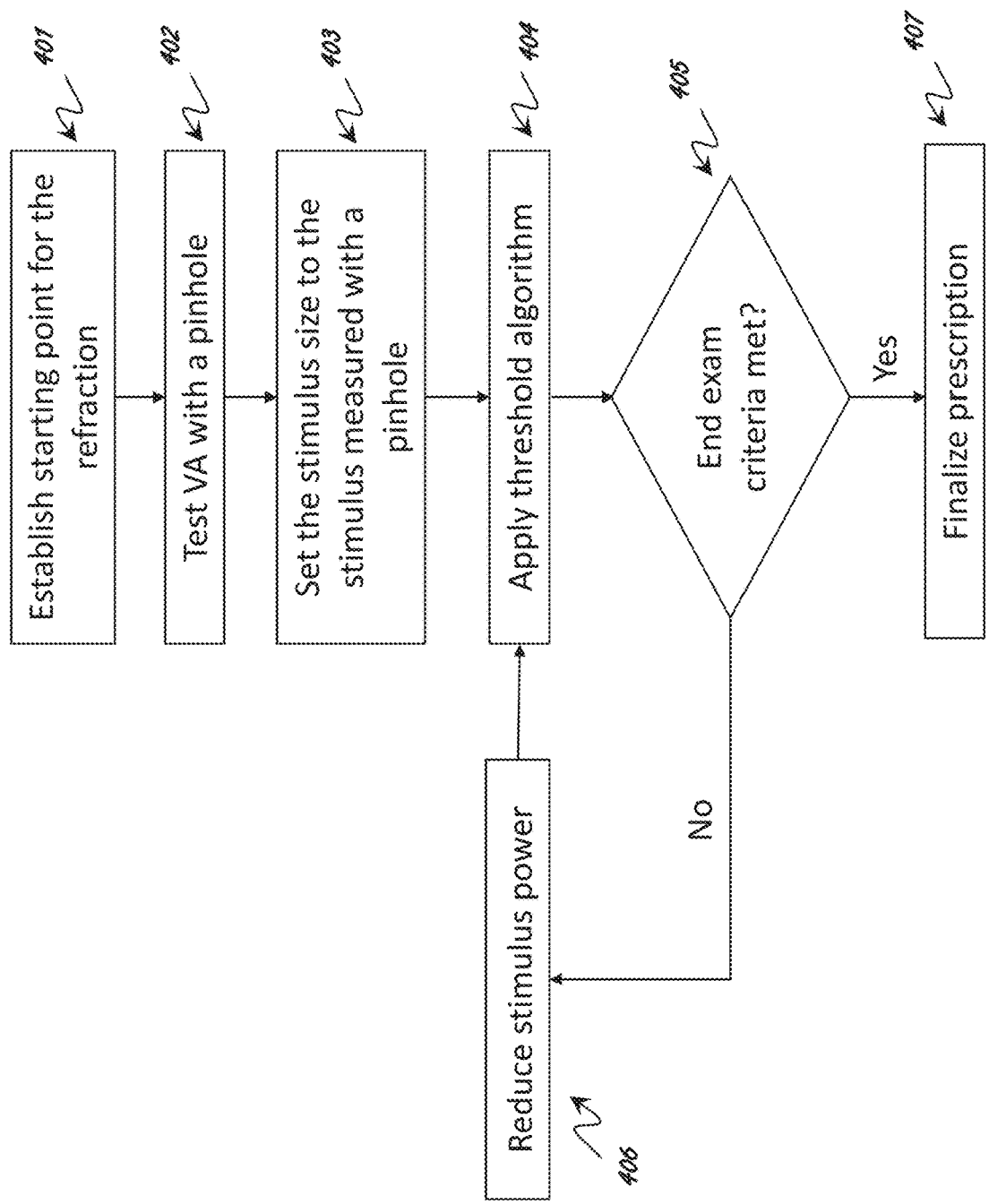
FIG. 4 is an illustration of a flow diagram of an automated phoropter examination for determination of refractive error correction utilizing pinhole measurement as a baseline.

Alternatively, the automated refraction measurement may be performed by estimating the BCVA using a pinhole method. Below is the possible sequence of steps utilizing such technique (FIG. 4):
1. Establish a starting point for the refraction using autorefractor reading, retinoscopy, or measurement of patient's spectacle power. 401
2. Test visual acuity with a pinhole using a threshold or another method. 402
3. Set the stimulus size to the threshold stimulus measured with the pinhole. 403
4. Use a threshold-based search algorithm with the variable being the power of the lens. The algorithm should converge at the prescribed sphere. 404
5. Reduce the stimulus size and refine the search with a few more presentations 406
6. Finalize prescription 407

In another aspect the patient may be allowed to manually adjust the lens power in the phoropter in order to optimize their vision. In such case a threshold VA may be found and then a subthreshold stimulus may be presented. The patient may then be allowed to vary the power of the phoropter lens by pressing up and down buttons with one hand. If the patient feels that his or her ability to see the stimulus is improving, they may continue changing the lens combination in the phoropter in a way that will continue improving the said patient's visual acuity. Once the patient can see the stimulus, a few more presentations may be needed to establish a new threshold. After that, another subthreshold value may be presented, and the patient may again start searching for the correct power to be able to see the stimulus. Once the BCVA is achieved, it may be impossible to further improve the patient's ability to see smaller stimuli.

The method described above may generate a table illustrating the dependence of the visual acuity on lens power. The actual prescription power may not necessarily be the power required to achieve BCVA, but it may also differ. This difference may be decided by the doctor, or it may be determined by a normative database of the visual performance.

In another aspect, a threshold-based method may be used to evaluate the visual acuity of black stimuli presented on red or green background. Based on the difference in the size threshold for these stimuli, the optimal power correction may be calculated and the power can be adjusted until the threshold stimuli on the red and green backgrounds are equal.

Conventionally, once the optimal power is established, the phoropter examination may be used to determine the cylinder power and axis. In the automated phoropter examination the patient may be allowed to optimize their own vision using a gamepad controller, or an alternative input device.

Figure 5:
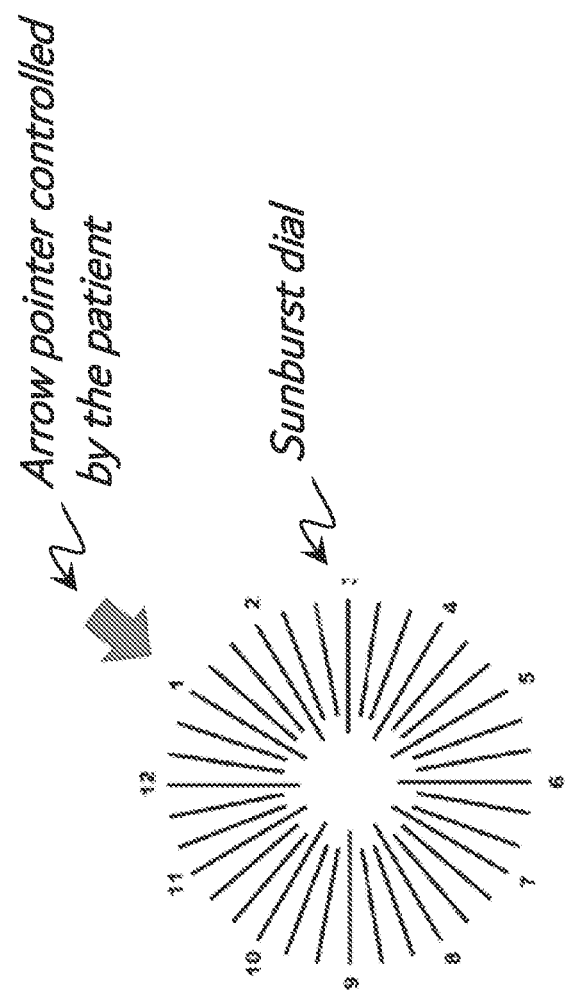
FIG. 5 is an illustration of a Sunburst dial with an arrow pointing to the darkest lines perceivable to the patient.

In one aspect of the invention the patient may use an Astigmatic Clock or Sunburst dial to first indicate the cylinder axis. In one exemplary aspect the patient may be asked to use the instrument controller to identify the darkest line in the Sunburst dial by positioning an arrow against it (FIG. 5). In such configuration the position of the said arrow may be controlled using one or more buttons, and the arrow may move around the dial as directed by the patient.

In another aspect one or several of the lines in the dial may be darker than others and patient may be asked to identify the darker lines by positioning the arrow against said darker lines. In such configuration the difference in the darkness or thickness of the lines may vary in such a way that a threshold-based identification of the cylinder axis and power is performed by the instrument.

In another aspect a Jackson Cross Cylinder may be used in a combination with automated threshold-based vision testing. In most simple exemplary case, the Jackson cross cylinder exam may be performed similar to the conventional subjective exam, with an exemption that instead of asking the patient which orientation of the Jackson cylinder gives a clearer vision, an actual threshold-based exam may be performed for each orientation.

In one example the patient may be asked to press the controller button that will allow them to rotate the cylinder to get the clearest vision. That may allow to determine the cylinder axis. After the cylinder axis is determined, the patient's acuity threshold may be measured with different orientation and powers of the Jackson cylinder in order to determine the cylinder power.

The invention claimed is:

1. A method of performing an optometric examination of a patient, the method comprising;
    positioning the patient behind a phoropter;
    presenting visual stimuli to the said patient using a computer-controlled device;
    allowing the patient to control the phoropter to try to find settings of the phoropter that allows the patient to see the stimuli;
    recording the patient's response to the said stimuli;
    automatically adjusting the settings of the said phoropter to improve one or more characteristics of the patient's vision;
    adjusting the characteristics of the visual stimuli presented on the computer-controlled device based on patient's input;
    finding a threshold at which the patient can see the stimuli;
    presenting the stimuli below the threshold;
    repeating to allow the patient to control the phoropter until there is no improvement in the one or more characteristics of the patient's vision; and
    automatically determining the prescription for the refractive error correction for the said patient.

2. The method in claim 1, wherein the patient's responses to the said stimuli are recorded through manual key inputs.

3. The method in claim 1, wherein the patient's responses to the said the said stimuli are recorded through voice commands.

4. The method in claim 1, wherein the said stimuli are represented by an object with varying orientation.

5. The method in claim 1, wherein the said stimuli are represented by a letter of the alphabet.

6. The method in claim 4, wherein the said stimuli are represented by Landolt C.

7. The method in claim 1, wherein the patient has an ability to control the lens combination in the phoropter.

8. The method of claim 7, wherein the patient has the ability to control the lens combination in the phoropter and provide responses to the stimuli.

9. The method of claim 1, wherein the patient has an ability to control the characteristics of the visual stimuli presented on the said computer-controlled device.

10. The method in claim 1, wherein the examination is conducted in a manner similar to a computer game, wherein during the examination patient is made aware of a specific score characterizing the vision of the said patient.

11. The method in claim 10, wherein the patient is tasked with maximizing the said score by providing correct responses to the stimuli and using the input device to vary the lens settings in the phoropter.

12. The method in claim 11, wherein the said score is related to visual acuity.

13. The method in claim 11, wherein the said score is related to contrast sensitivity.

14. The method in claim 11, wherein the said score is derived from measuring a certain output of the psychometric function of the said patient.

15. The method of claim 14, wherein the said score is related to the threshold value of the presented stimulus.

16. The method of claim 14, wherein the said score is related to the slope value of the presented stimulus.

17. The method of claim 1, wherein the automatic determination of the prescription correction includes:
    sphere power; and
    cylinder power and orientation of the refractive error.

18. The method of claim 17, wherein the cylinder orientation is measured by presenting an astigmatic clock or Sunburst dial to the patient.

19. The method of claim 17, wherein the patient is tasked with identifying a non-symmetric feature on the symmetric stimulus.

20. The method of claim 17, wherein the presented stimulus is non-symmetric and the patient is tasked with identifying the orientation of the asymmetric feature in the stimulus.

* * * * *